United States Patent [19]

McRae

[11] Patent Number: Plant 6,422

[45] Date of Patent: Nov. 29, 1988

[54] LILY NAMED BUTTER PIXIE

[75] Inventor: Edward A. McRae, Boring, Oreg.

[73] Assignee: Melridge, Inc., Gresham, Oreg.

[21] Appl. No.: 6,026

[22] Filed: Jan. 22, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant of short, thirty-five to forty centimeter stature, bearing large clusters of medium to large size upright flowers, particularly characterized by their vivid yellow coloration and virtual spotlessness, this combination of features making this plant especially suitable as a pot plant variety. The color pattern and silhouette of this new plant are completely new in the upright Asiatic divisions of lilies suited to forcing and to mass commercial cultivation. The plant is highly resistant to disease and shows high tolerance of virus, maing is an excellent garden plant, and the bulbs may be precooled and forced throughout the year for pot plant production. The clone is vigorous and a good grower and propagator.

1 Drawing Sheet

BACKGROUND OF THE NEW PLANT

This new variety of lily plant originated as a seedling selected from a group of seedlings planted by me at Sandy, Oreg., and resulting from my crossing a very short, cream-flowered clonal selection from the 'pastel hybrids' strain as the seed parent and, as the pollen parent, a golden yellow-flowered seedling from a cross of 'Connecticut Lemonglow'×'Red Carpet', the object of my crossing being the production of lilies in shades of yellow well suited to forcing for pot plant production out of season, heretofore unknown in the lily breeding art.

Propagation of this new variety was carried on by me and my associates through several successive generations, wherefrom we found that the variety remains short and is not overly susceptible to bud abortion when forced into flower out of season as a pot plant; and in addition, we found that the clone possesses to a high degree the desirable characteristics of hybrid vigor, great hardiness, and disease resistance, as well as all of the desired characteristics of excellence of form, color, and habit.

We found that this new variety is well suited to forcing out of season when the bulbs are dug at the appropriate time and properly precooled; October-dug bulbs, properly precooled and potted in January, will flower under glass in western Oregon in an average of seventy to seventy-five days, with no supplemental lighting and at moderate greenhouse temperatures. Our experience with this new variety has demonstrated that its novel and distinctive characteristics hold true under asexual propagation from generation to generation, and are well fixed.

DESCRIPTION OF THE DRAWING

This new variety of lily plant is illustrated in the accompanying photographic drawing, which shows a full face view of a fully opened bloom in full color and illustrates the flower form and tepal arrangement, the colors shown being as nearly true to those specified herein as is reasonably possible to obtain by conventional professional photographic procedures.

DESCRIPTION OF THE NEW PLANT

The following is a detailed description of my new variety of Asiatic hybrid lily based upon observation of plants grown at Sandy, Oreg., during the middle of 1986, the color designations being according to The R.H.S. Colour Chart published in 1966 by The Royal Horticultural Society of London, England.

THE PLANT

Origin: Seedling.

Parentage:

*Seed parent.*—A short, cream-flowered Lilium pastel hybrid clonal selection.

*Pollen parent.*—A golden yellow-flowered Lilium hybrid selection from 'Connecticut Lemonglow'×'Red Carpet'.

Classification:

*Botanic.*—Division I-A, upright Asiatic hybrid lily, according to the Horticultural Classification of Lilies, Royal Horticultural Society of London, England.

*Commercial.*—Hybrid Lilium Clone.

Form: Single stem, erect and stately.

Height: About 35 to 40 cm. for stems produced by glasshouse forcing of bulbs of about 12 to 18 cm. in circumference with adequate light levels. Low light levels may cause "stretching".

Growth: Vigorous and upright.

Foliage:

*Quantity.*—Abundant.

*Leaf size.*—About 8 to 12 cm. long and about 1 cm. wide.

*Leaf shape.*—Lanceolate with acuminate tip.

*Texture.*—Leathery.

*Aspect.*—Glossy; lightly pubescent along the margin and the leaf axils.

*Color.*—Dark green, somewhat lighter on the bottom side.

The bulb:

*Size.*—Various, according to age, ranging to 25 cm. in circumference in commercial use.

*Color.*—White.

THE BUD

Form: Long ovoid and obtuse at base and tip.

Size: About 8 to 9 cm. long and about 5 cm. in circumference just prior to opening.

Opening rate: The bud opens slowly, taking about one hour in response to morning light.

Color: Clear yellow with green apex just prior to opening and as the tepals begin to unfurl.

Peduncle:

*Length.*—About 4 to 8 cm., in average. The peduncle may elongate if light levels are too low or if bulbs have been improperly stored prior to forcing.

*Color.*—Dark green with deep plum overlay.

THE FLOWER

Blooming habit: Once annually, and flowering profusely in midseason.

Size: The flowers average about 13 to 18 cm. in diameter.

Borne: In a single compact raceme producing 5 to 9 buds from a bulb of about 12 to 16 cm. in circumference.

Shape: Cup-shaped when bloom first opens and becoming flatter as the tepals recurve during the second day.

Tepalage: Normal, with six imbricated tepals in hexagonal arrangement.

*Color.*—The base color is yellow, 12A, shading to 14A-B at the extreme tepal margins and tips. The nectaries are green with white pubescence.

*Spotting.*—There are a few tiny, inconspicuous spots parallel with the nectaries and some colorless papillae along the nectary margins.

*Appearance.*—The flower is shiny.

*Tepal longevity.*—The tepals stay on the stem about three weeks.

Pedicel:

*Length.*—Averages about 4 to 8 cm.

*Character.*—Sturdy and ascending up to sixty degrees from the horizontal and very rarely having secondary buds.

*Color.*—Dark green with soft plum overlay.

Color changes: The flower color deepens to 13A as the flower ages and if the light levels are adequate for cut flower and pot plant maintenance.

Disease resistance: The flower and plant are resistant to disease and in particular, they are resistant to Fusarium bulb rot and Botrytis blight.

Lasting quality: The flower is long lasting both on the plant and as a cut flower.

REPRODUCTIVE ORGANS

Stamens:

*Number.*—Six, with arrangement typical of genus Lilium.

*Anthers and pollen.*—Color: Greyed orange, 167A.

*Filaments.*—Length: About 5 cm. Color: Soft cream, 12D.

Pistil:

*Number.*—One.

*Length.*—About 5 cm.

*Stigma.*—Size: Medium. Color: Deep magenta-plum.

Character of ovary: The ovary is characteristic of genus Lilium.

THE FRUIT

Fertility: The fruit is fertile.

Shape: Ovoid.

Color at maturity: Soft brown, sometimes overlaid with soft plum.

This new lily variety most closely resembles the variety 'Sunray' but it has upright, virtually unspotted flowers, a higher bud count, a more compact inflorescence, a shorter height, and longer leaves. The new variety is also more reliable and uniform in its forcing performance than 'Sunray'.

I claim:

1. A new and distinct variety of Asiatic hybrid lily, substantially as herein shown and described, characterized by its short height and its medium-large sized, vivid yellow flowers; the excellence of its flower form and its versatility both as a garden plant and as a pot plant variety well suited to forcing into flower out of season.

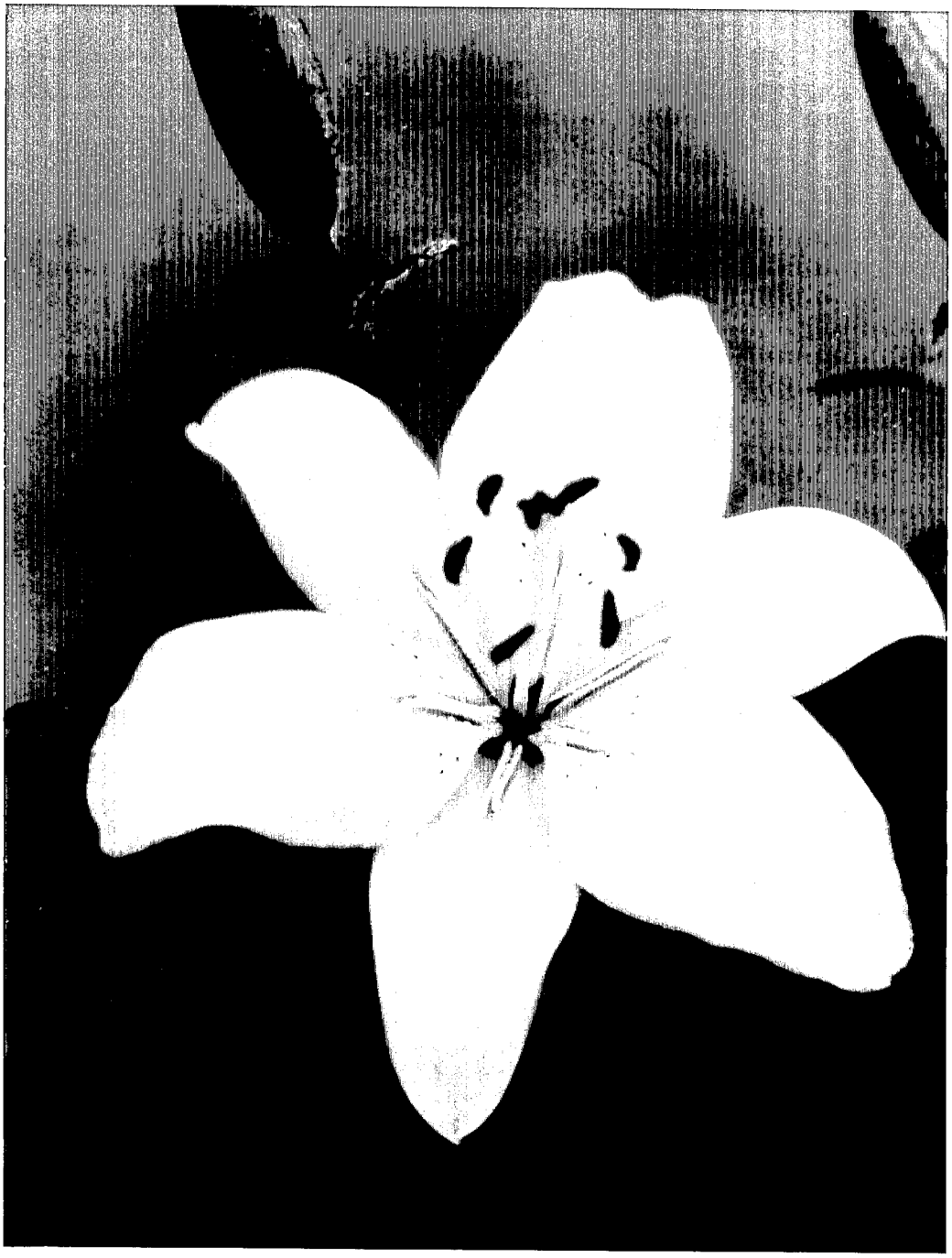

* * * * *